United States Patent [19]

Dowle et al.

[11] Patent Number: 5,023,378
[45] Date of Patent: Jun. 11, 1991

[54] AMINE DERIVATIVES

[75] Inventors: Michael D. Dowle; David Middlemiss; Harry Finch; Alan Naylor; Lawrence H. C. Lunts, all of Hertfordshire, England

[73] Assignee: Glaxo Group Limited, England

[21] Appl. No.: 418,208

[22] Filed: Oct. 6, 1989

Related U.S. Application Data

[63] Continuation of Ser. No. 226,199, Jul. 29, 1988, abandoned, which is a continuation of Ser. No. 932,301, Nov. 19, 1986, abandoned, which is a continuation of Ser No. 818,694, Jan. 14, 1986, abandoned.

[30] Foreign Application Priority Data

Jan. 15, 1985 [GB] United Kingdom ............ 8500926
Jan. 15, 1985 [GB] United Kingdom ............ 8500927

[51] Int. Cl.$^5$ .............. C07C 321/00; C07C 323/00;
C07C 381/00; C07C 215/00
[52] U.S. Cl. .................................. 564/340; 564/341;
564/361; 564/367
[58] Field of Search .............. 564/340, 341, 361, 367;
514/545, 653, 654

[56] References Cited

U.S. PATENT DOCUMENTS

| | | | |
|---|---|---|---|
| 2,653,977 | 9/1953 | Craig et al. | 564/367 |
| 3,329,709 | 7/1967 | Schmid et al. | 564/361 |
| 3,673,187 | 6/1972 | Schromm et al. | 564/361 |
| 3,789,072 | 1/1974 | Bernstein | 564/341 |
| 4,024,281 | 5/1977 | Colella et al. | 564/367 |
| 4,134,996 | 1/1979 | Dunbar et al. | 564/341 |
| 4,657,929 | 4/1987 | Ince et al. | 514/524 |

FOREIGN PATENT DOCUMENTS

| | | |
|---|---|---|
| 0072061 | 2/1983 | European Pat. Off. |
| 987438 | 3/1965 | United Kingdom |
| 1475375 | 6/1977 | United Kingdom |

Primary Examiner—Nathan M. Nutter
Attorney, Agent, or Firm—Bacon & Thomas

[57] ABSTRACT

The invention provides compounds of the general formula (I)

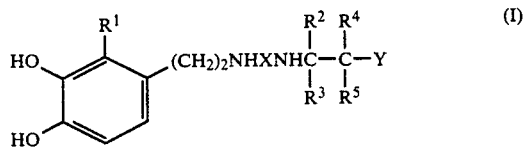

and physiologically acceptable acid addition salts, metabolically labile esters and solvates thereof in which $R^1$ represents a halogen atom or a methyl, ethyl, n-propyl or n-butyl group;

$R^2$, $R^3$, $R^4$ and $R^5$ each represent hydrogen atoms or one or two of $R^2$, $R^3$, $R^4$ and $R^5$ represent a methy or ethyl group;

X represents a $C_{4-7}$ alkylene chain optionally substituted by one or more $C_{1-4}$ alkyl or hydroxyl groups; or optionally containing one or two double or triple bonds; or optionally interrupted by an oxygen or sulphur atom, or by a sulphone (—$SO_2$—) or urea (—NHCONH—) group; and Y represents a phenyl ring optionally carrying one to three substituents selected from hydroxyl, $C_{1-4}$ alkyl, $C_{1-4}$ alkoxy, amino, carboxamido, $C_{1-4}$ alkylsulphonylamino and nitro groups and halogen atoms with the proviso that when X is a $C_{4-7}$ alkylene chain optionally containing one double bond then Y cannot represent phenyl or phenyl carrying one substituent which is halogen.

The compounds according to the invention decrease total peripheral vascular resistance, increase cardiac output and produce a fall in blood pressure. They may be used in the treatment or prophylaxis of renal insufficiency and cardiovascular disorders such as hypertension, ischaemic heart disease or heart failure, for example acute or congestive heart failure.

12 Claims, No Drawings

AMINE DERIVATIVES

This application is a continuation of application Ser. No. 226,199 filed Jul. 29, 1988 (now abandoned); which is a continuation of application Ser. No. 932,301 filed Nov. 19, 1986 (now abandoned); which is a continuation of application Ser. No. 818,694 filed Jan. 14, 1986 (now abandoned).

This invention relates to amine derivatives, processes for their preparation and pharmaceutical compositions containing them. More particularly it relates to 2-substituted-3,4-dihydroxyphenethylamino derivatives having pharmacological activity.

According to the invention we provide compounds of the general formula (I):

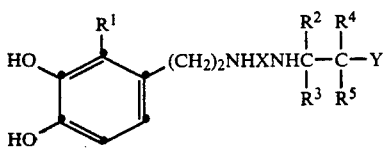

and physiologically acceptable acid addition salts, metabolically labile esters and solvates (e.g. hydrates) thereof in which $R^1$ represents a halogen atom or a methyl, ethyl, n-propyl or n-butyl group;

$R^2$, $R^3$, $R^4$ and $R^5$ each represent hydrogen atoms or one or two of $R^2$, $R^3$, $R^4$ and $R^5$ represent a methyl or ethyl group;

X represents a $C_{4-7}$ alkylene chain optionally substituted by one or more $C_{1-4}$ alkyl or hydroxyl groups; or optionally containing one or two double or triple bonds; or optionally interrupted by an oxygen or sulphur atom, or by a sulphone (—$SO_2$—) or urea (—NHCONH—) group; and Y represents a phenyl ring optionally carrying one to three substituents selected from hydroxyl, $C_{1-4}$ alkyl, $C_{1-4}$ alkoxy, amino, carboxamido, $C_{1-4}$ alkylsulphonylamino and nitro groups and halogen atoms with the proviso that when X is a $C_{4-7}$ alkylene chain optionally containing one double bond then Y cannot represent phenyl or phenyl carrying one substituent which is halogen.

Where optical isomers may exist formula (I) is intended to cover all enantiomers, diastereoisomers and mixtures thereof including racemates. Compounds containing one or two double bonds in the alkylene chain X may exist in the cis or trans configuration.

Within the above definition the term 'alkyl' as a group or part of a group means that the group is straight or branched. The term 'halogen' means a fluorine, chlorine, bromine or iodine atom.

Examples of the group X include —$(CH_2)_5$—, —$(CH_2)_6$—, —$(CH_2)_7$—, —$(CH_2)_3O(CH_2)_3$—, —$(CH_2)_4O(CH_2)_2$—, —$(CH_2)_3CHOH(CH_2)_3$—, —$(CH_2)_2CHMe(CH_2)_3$—, $(CH_2)_3S(CH_2)_3$—, —$(CH_2)_3SO_2(CH_2)_3$—, —$CH_2CH=CH(CH_2)_3$—, —$(CH_2)_2CH=CH(CH_2)_2$—, —$CH_2CH=CHCH=CHCH_2$—, —$(CH_2)_2C\equiv C(CH_2)_2$—, —$CH_2C\equiv C(CH_2)_3$— and —$(CH_2)_2NHCONH(CH_2)_2$—.

Preferred compounds of the invention are those in which the group $R^1$ is a chlorine atom, or more preferably a $C_{1-2}$ alkyl group, particularly an ethyl group.

$R^2$ and $R^3$, which may be the same or different, preferably represent a hydrogen atom or a methyl group, or more preferably $R^2$, $R^3$, $R^4$ and $R^5$ each represent a hydrogen atom.

Further preferred compounds are those in which X represents a $C_{5-7}$ alkylene chain, or more preferably a $C_6$ or $C_7$ alkylene chain. When X represents a $C_{5-7}$ alkylene chain this is most preferably —$(CH_2)_6$—.

Another group of preferred compounds are those in which X represents a $C_{5-7}$ alkylene chain substituted by one alkyl (e.g. methyl) group or a hydroxy group, or a $C_6$ alkylene chain containing one or two double bonds, or a $C_6$ alkylene chain interrupted by an oxygen or sulphur atom or by a sulphone (—$SO_2$—) group. Particularly preferred compounds are those in which X represents —$(CH_2)_3S(CH_2)_3$ or, more preferably, —$(CH_2)_3SO_2(CH_2)_3$—.

Y preferably represents a group of formula (II)

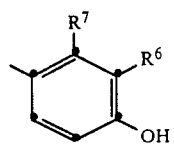

where $R^6$ represents a hydrogen atom or a group $CONH_2$ and $R^7$ is hydrogen, or more preferably $R^6$ represents a hydroxyl group and $R^7$ is a hydrogen or halogen (e.g. chlorine) atom or a $C_{1-4}$ alkyl (e.g. methyl or ethyl) group. Particularly preferred compounds are those of formula (II) in which $R^6$ represents a hydroxyl group and $R^7$ is a methyl or ethyl group.

One group of preferred compounds are those in which X represents a $C_{5-7}$ alkylene chain and Y is a group of formula (IIa)

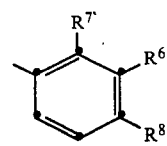

where $R^6$ and $R^8$, which may be the same or different, each represent a hydrogen atom or a hydroxy group (provided that at least one of $R^6$ and $R^8$ represent hydroxy) and $R^7$ represents a hydrogen atom or a halogen atom, preferably a chlorine atom, or a $C_{1-4}$ alkyl group, preferably a methyl or ethyl group.

Another group of preferred compounds are those in which X represents a $C_{5-7}$ alkylene chain substituted by one alkyl (e.g. methyl) group or a hydroxyl group, or a $C_6$ alkylene chain containing one or two double bonds, or a $C_6$ alkylene chain interrupted by an oxygen or sulphur atom or by a sulphone (—$SO_2$—) group, and Y is a group of formula (IIb)

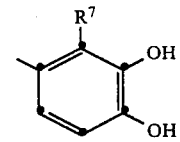

where $R^7$ represents a hydrogen or halogen atom e.g. a chlorine atom or, more preferably, a $C_{1-4}$ alkyl group, particularly an ethyl group.

According to one aspect the invention provides compounds of formula (I) in which $R^1$ represents a methyl, ethyl, n-propyl or n-butyl group, $R^2$, $R^3$, $R^4$ and $R^5$ each represent hydrogen atoms or one or two of $R^2$, $R^3$, $R^4$ and $R^5$ represent a methyl or ethyl group, X represents a $C_{5-7}$ alkylene chain, and Y represents a phenyl ring carrying one to three substituents selected from hydroxyl, $C_{1-4}$ alkyl, $C_{1-4}$ alkoxy, amino and nitro groups and halogen atoms with the proviso that Y cannot represent phenyl carrying one substituent which is halogen.

According to a further aspect the invention provides compounds of formula (I) in which $R^1$ represents a fluorine, chlorine, bromine or iodine atom, $R^2$, $R^3$, $R^4$ and $R^5$ each represent hydrogen atoms or one or two of $R^2$, $R^3$, $R^4$ and $R^5$ represent a methyl or ethyl group, X represents a $C_{5-7}$ alkylene chain, and Y represents a phenyl ring carrying one to three substituents selected from hydroxyl, $C_{1-4}$ alkyl, $C_{1-4}$ alkoxy, amino and nitro groups and halogen atoms with the proviso that Y cannot represent phenyl carrying one substituent which is halogen.

The physiologically acceptable acid addition salts of the compounds of formula (I) may be derived from inorganic or organic acids. Examples of such salts include hydrochlorides, hydrobromides, sulphates, phosphates, benzoates, p-toluenesulphonates, methanesulphonates, sulphamates, ascorbates, tartrates, citrates, maleates, salicylates, fumarates, succinates, lactates, glutarates, glutaconates, acetates or tricarballytates.

Preferred acid addition salts are the hydrochlorides and hydrobromides.

Physiologically acceptable metabolically labile ester derivatives may be formed by acylation, for example of any of the hydroxyl groups in the parent compound of general formula (I), with prior protection of any other reactive groups present in the molecule. Examples of such esters include lower alkanoates such as acetates or pivaloates. In addition to the above ester derivatives the present invention includes within its scope compounds of general formula (I) in the form of other physiologically acceptable equivalents, i.e. physiologically acceptable compounds which like the metabolically labile esters are converted in vivo into the parent compounds of general formula (I). The invention also includes within its scope the solvates, especially the hydrates of compounds of general formula (I).

Tests in animals have shown that compounds according to the invention at low dosages decrease total peripheral vascular resistance, increase cardiac output and produce a fall in blood pressure. Compounds according to the invention have a long duration of action and are active following oral administration.

We have found that compounds according to the invention are more potent stimulators of vascular dopamine receptors than neuronal dopamine receptors.

Compounds according to the invention also stimulate $\beta$-adrenoceptors.

Particularly preferred compounds according to the invention are:

4,4'-[sulphonylbis[(3,1-propanediylimino)-2,1-ethanediyl]]bis[3-ethyl-1,2-benzenediol];

4,4'-[thiobis[(3,1-propanediylimino)-2,1-ethanediyl]]bis[3-ethyl-1,2-benzenediol];

4,4'-[1,6-hexanediylbis(imino-2,1-ethanediyl)]bis[3-ethyl-1,2-benzenediol]; and

4-[2-[[6-[[2-(3,4-dihydroxy-2-methylphenyl)ethyl]amino]hexyl]amino]ethyl]-3-ethyl-1,2-benzenediol and their physiologically acceptable salts e.g. their hydrobromides and hydrochlorides.

Compounds of the invention may be used in the treatment or prophylaxis of renal insufficiency and cardiovascular disorders such as hypertension, ischaemic heart disease or heart failure, for example acute or congestive heart failure.

The compounds of formula (I) and their physiologically acceptable acid addition salts, solvates and metabolically labile esters may be formulated for administration in any convenient way, and the invention also includes within its scope pharmaceutical compositions comprising at least one compound of formula (I) or a physiologically acceptable salt, solvate or metabolically labile ester thereof adapted for use in human or veterinary medicine. Such compositions may be presented for use in conventional manner in admixture with one or more physiologically acceptable carriers or excipients.

Thus, the compounds according to the invention may be formulated for oral, buccal, parenteral or rectal administration or in a form suitable for administration by inhalation or insufflation. Oral administration is preferred.

Tablets and capsules for oral administration may contain conventional excipients such as binding agents, for example mucilage of starch or polyvinylpyrrolidone; fillers, for example, lactose, microcrystalline cellulose or maize-starch; lubricants, for example, magnesium stearate or stearic acid; disintegrants, for example, potato starch, croscarmellose sodium or sodium starch glycollate; or wetting agents such as sodium lauryl sulphate. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, for example, sorbitol syrup, methyl cellulose, glucose/sugar syrup or carboxymethyl cellulose; emulsifying agents, for example, sorbitan monooleate; non-aqueous vehicles (which may include edible oils), for example, propylene glycol or ethyl alcohol; and preservatives, for example, methyl or propyl p'-hydroxybenzoates or sorbic acid. The compounds or their salts or esters may also be formulated as suppositories, e.g. containing conventional suppository bases such as cocoa butter or other glycerides. For buccal administration the composition may take the form of tablets or lozenges formulated in conventional manner.

The compounds of formula (I) and their physiologically acceptable acid addition salts and metabolically labile esters may be formulated for parenteral administration by bolus injection or continuous infusion and may be presented in unit dose form in ampoules, or in multi-dose containers with an added preservative. The compositions may take such forms as suspensions, solutions, or emulsions in oily or aqueous vehicles, and may contain formulatory agents such as suspending, stabilising and/or dispersing agents. Alternatively the active ingredient may be in powder form for constitution with a suitable vehicle, e.g. sterile, pyrogen-free water, before use.

For administration by inhalation the compounds according to the invention are conveniently delivered in the form of an aerosol spray presentation from pressurised packs or a nebuliser, with the use of a suitable propellant, e.g. dichlorodifluoromethane, trichlorofluoromethane, dichlorotetrafluoroethane or other suitable gas. In the case of a pressurised aerosol the dosage unit may be determined by providing a valve to deliver a metered amount.

Alternatively, for administration by inhalation or insufflation, the compounds according to the invention may take the form of a dry powder composition, for example a powder mix of the compound and a suitable powder base such as lactose or starch. The powder composition may be presented in unit dosage form in, for example, capsules or cartridges of e.g. gelatin, or blister packs from which the powder may be administered with the aid of an inhaler or insufflator.

When the compositions comprise dosage units, each unit will preferably contain 5 mg to 500 mg, advantageously where the compounds are to be administered orally 25 mg to 400 mg of the active compound. The daily dosage as employed for adult human treatment will preferably range from 5 mg to 3 g, most preferably from 25 mg to 1 g which may be administered in 1 to 4 daily doses, for example, depending on the route of administration and on the condition of the patient.

The compounds of formula (I) and their physiologically acceptable acid addition salts and metabolically labile esters may be administered in combination with other therapeutic agents such as beta-blockers, diuretics, angiotensin converting enzyme inhibitors, inotropic agents and antiemetics.

The compounds of the invention may be prepared by a number of processes as described in the following wherein $R^2$-$R^5$ and X are as defined for general formula (I) unless otherwise stated, $R^9$ and $R^{10}$ each represent a hydrogen atom or a protecting group, $Y^1$ is the group Y as previously defined for general formula (I) or a protected form thereof and Ar represents the group

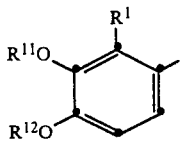

wherein $R^1$ is as defined for general formula (I) and $R^{11}$ and $R^{12}$ each represent a hydrogen atom or a protecting group. It will be appreciated that certain of the reactions described below are capable of affecting other groups in the starting materials which are desired in the end product; this applies especially in the reduction processes described, particularly where a hydride reducing agent is used and end products are required in which Y is a carboxamido substituted phenyl ring or X contains a urea group, and where hydrogen and a metal catalyst are used in the preparation of compounds containing an ethylene or acetylene linkage. Care must therefore be taken in accordance with conventional practice, either to use reagents which will not affect such groups, or to perform the reaction as part of a sequence which avoids their use when such groups are present in the starting material.

According to one general process (1) the compounds of general formula (I) may be prepared by reduction of a compound of formula (III)

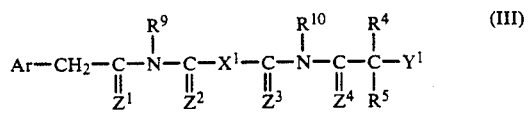

wherein $X^1$ is a $C_{2-5}$ alkylene chain optionally substituted by one or more alkyl or hydroxy groups, or optionally containing one or two double or triple bonds or a carbonyl group, or optionally interrupted by an oxygen or sulphur atom or a sulphone ($-SO_2-$) or urea ($-NHCONH-$) group, and $Z^1$, $Z^2$, $Z^3$ and $Z^4$ each represent 0, or the groups $C=Z^1$, $C=Z^2$ and $C=Z^3$ each represent the group $CH_2$ and $C=Z^4$ may be the group $CR^2R^3$, providing that at least one but no more than two of the groups $Z^1$, $Z^2$, $Z^3$ and $Z^4$ represent 0 and when $Z^1$ is 0, $C=Z^2$ is the group $CH_2$ and when $Z^3$ is 0, $C=Z^4$ is the group $CR^2R^3$, the reduction being followed, where necessary, by removal of any protecting group.

The reducing agents which may be used are those generally known for the reduction of amides. Suitable reducing agents for this reaction are hydrides such as lithium aluminium hydride, alane or diborane. Suitable solvents include ethers such as tetrahydrofuran or dioxan or a mixture of a hydrocarbon (e.g. benzene) and an ether (e.g. diethyl ether). The reduction may conveniently be carried out at any temperature from $-20°$ C. to $+100°$ C., preferably $0°$ to $70°$ C.

According to another general process (2) compounds of general formula (I) may be prepared by an alkylation reaction involving compounds of formulae (IV) and (V)

and an alkylating agent capable of introducing the group X, followed where necessary by removal of any protecting groups.

Thus, in one embodiment of the process compounds of formulae (IV) and (V) may be reacted with an alkylating agent of formula L-X-L (where L is a readily displaceable atom or group) to give compounds of the invention.

The reaction is preferably carried out in the presence of a base such as potassium carbonate or sodium hydride, and in solution at a temperature in the range $-20°$ C. to $+100°$ C. Suitable reaction solvents include ethers e.g. tetrahydrofuran or dioxan; alcohols e.g. ethanol; acetonitrile; substituted amides, e.g. N,N-dimethylformamide and hydrocarbons, e.g. benzene.

L may be, for example, a halogen atom such as chlorine, bromine or iodine, or a hydrocarbylsulphonyloxy group such as methanesulphonyloxy or p-toluenesulphonyloxy.

In a further embodiment of the alkylation process compounds of formulae (IV) and (V) in which $R^9$ and $R^{10}$ represent hydrogen may be alkylated with a compound of formula $OHC-X^1-CHO$ (where $X^1$ is as defined previously) under reducing conditions to give compounds of formula (I).

Suitable reducing agents include an alkali metal or alkaline earth metal borohydride or cyanoborohydride such as sodium borohydride or cyanoborohydride, using an alcohol such as ethanol or propanol as solvent; or hydrogen in the presence of a metal catalyst such as, platinum, platinum oxide, palladium or rhodium using an alcohol e.g. ethanol, an ether e.g. dioxan, or an ester e.g. ethyl acetate as reaction solvent. The catalyst may be supported on, for example, charcoal or a homogenous catalyst such as tris-triphenylphosphinerhodium chloride may be used. The reduction may conveniently be carried out at a temperature from $-20°$ C. to $+100°$ C., preferably $0°$ to $50°$ C. It may be possible under certain conditions to isolate any intermediate imine compound which may be formed. Reduction of the imine using the conditions described above followed where necessary by removal of any protecting groups gives a compound of general formula (I).

According to another general process (3) compounds of the formula (I) may be prepared by deprotection of compounds of formula (VI).

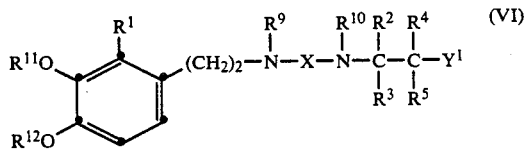

where at least one of $R^9$, $R^{10}$, $R^{11}$, $R^{12}$ represents a protecting group and/or the group $Y^1$ is in a protected form.

When $R^9$, $R^{10}$, $R^{11}$ or $R^{12}$ is a protecting group it may be any conventional protecting group, for example, as described in "Protective Groups in Organic Chemistry", Ed. J. F. W. McOmie (Plenum Press 1975). Examples of suitable hydroxyl protecting groups represented by $R^{11}$ and $R^{12}$ are alkyl groups such as methyl or methoxymethyl, arylmethyl groups such as benzyl, diphenylmethyl or triphenylmethyl, and heterocyclic groups such as tetrahydropyranyl and acyl groups such as acetyl. It will be appreciated that $R^{11}$ and $R^{12}$ may together form a protecting group for both hydroxyl groups, for example an alkylene group such as methylene. Where the right-hand side of the molecule contains two hydroxy groups they may be similarly protected. Examples of suitable amine protecting groups represented by $R^9$ and $R^{10}$ are trifluoroacetyl, t-butoxycarbonyl, trifluoroethoxycarbonyl, benzyl, benzyloxycarbonyl and 2,2,2-trichloroethoxycarbonyl groups.

The protecting groups $R^9$, $R^{10}$, $R^{11}$ and $R^{12}$ may be removed using conventional techniques to yield a compound of formula (I). Thus, for example, an arylmethyl group such as benzyl may be cleaved by hydrogenolysis in the presence of a noble metal catalyst (e.g. palladium on charcoal); an alkyl group protecting a hydroxyl group or an alkylenedioxy group protecting two hydroxyl groups may be cleaved under acidic conditions e.g. with hydrogen bromide or boron tribromide and an acyl group may be removed by hydrolysis under basic conditions.

Compounds of formula (I) in which Y represents a phenyl ring containing a carboxamido group may be prepared by aminating the corresponding carboxylic acid ester. The amination will generally be effected using ammonia in an organic solvent such as an alcohol e.g. methanol or ethanol at a temperature in the range $0°$ to $150°$, preferably at room temperature. It may also be desirable to carry out the reaction at high pressure. The carboxylic acid ester precursor may be prepared according to the method of general process (2).

When it is desired to prepare a physiologically acceptable salt of a compound of formula (I), the product of any of the above procedures may be converted into a salt by treatment of the resulting free base with a suitable acid using conventional methods.

Physiologically acceptable salts may also be prepared from other salts, including other physiologically acceptable salts, of the compounds of formula (I) using conventional methods.

Enantiomers of the compounds of the invention may be obtained by resolution of the corresponding racemic compound using conventional means, such as an optically active resolving acid; see for example "Stereochemistry of Carbon Compounds" by E L Eliel (McGraw Hill 1962) and "Tables of Resolving Agents" by S H Wilen.

The methods just described for preparing the compounds of the invention can each be used as the last main step in a preparative sequence. The same general methods can be used for the introduction of the desired groups at an intermediate stage in the stepwise formation of the required compound, and it will be appreciated that these general methods can be combined in different ways in such a multi-stage process.

Compounds of formula (III) can be built up by one or more acylation reactions which involve the reaction of an appropriate amine with an appropriate acylating agent. In the following discussion $Z^1$, $Z^2$, $Z^3$, $Z^4$ and $X^1$ are as defined in formula (III) except where otherwise stated.

Thus for example compounds of formula (III) in which $Z^1$ is oxygen may be prepared by reaction of a compound of formula (VII) or a reactive derivative thereof with a compound of formula (VIII)

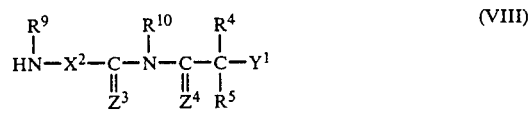

(where $X^2$ represents a $C_{3-6}$ alkylene chain optionally substituted by one or more alkyl or hydroxyl groups, or optionally containing one or two double or triple bonds, or optionally interrupted by an oxygen or sulphur atom or a sulphone ($-SO_2-$) or urea ($-NHCONH-$) group.

Compounds of formula (III) where $Z^2$ is oxygen may be prepared by reaction of a compound of formula (IV) with a compound of formula (IX)

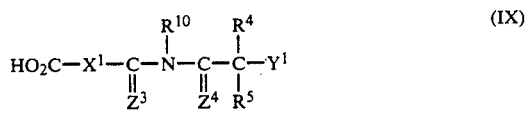

or a reactive derivative thereof.

Compounds of formula (III) in which $Z^3$ is oxygen may be prepared by reaction of a compound of formula (V) with a compound of formula (X)

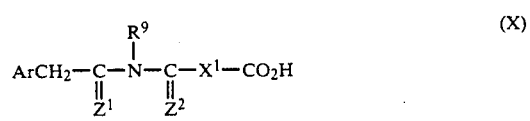

or a reactive derivative thereof.

Compounds of formula (III) in which $Z^4$ is oxygen may be prepared by reaction of a compound of formula (XI) with a compound of formula (XII) or a reactive derivative thereof

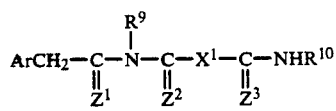

HO₂CCR⁴R⁵Y¹ (XII)

Compounds of formula (III) in which $Z^2$ and $Z^3$ are oxygen may be prepared by reacting a compound of formula $HO_2C$—$X^1$—$CO_2H$ (XIII) or a reactive derivative thereof with compounds of formulae (IV) and (V)

Compounds of formula (III) where $Z^1$ and $Z^4$ are oxygen may be prepared by reacting compounds of formulae (VII) and (XII) or reactive derivatives thereof with a compound of formula $HR^9N$—X—$NHR^{10}$ (XIV).

Suitable reactive derivatives of carboxylic acids used in the acylation reactions described above include acid halides, e.g. acid chlorides or bromides or anhydrides or active esters. Acylation with an acid halide may be effected in the presence of an acid binding agent such as an organic base e.g. a tertiary amine such as triethylamine, or an inorganic base such as potassium carbonate. Acylation using the free acid is desirably conducted in the presence of a coupling agent for example a carbodiimide such as N,N'-dicyclohexylcarbodiimide, a carbonyl compound such as N,N'-carbonyldiimidazole, or an azide such as diphenylphosphorylazide. The reaction medium is desirably an anhydrous medium such as a halogenated hydrocarbon e.g. dichloromethane or an amide e.g. dimethylformamide. Acylation may be effected at temperatures of from $-20°$ to $+50°$ C.

A number of compounds of general formula (VII) are known and may be prepared by conventional means. Other compounds of formula (VII) may be prepared by hydrolysis of compounds of formula $ArCH_2CN$ (XV) using conventional reaction conditions, for example base hydrolysis.

Compounds of formula (VIII) where $Z^4$ is oxygen may be prepared by reacting a compound of formula (XII) or a reactive derivative thereof, with a compound of formula (XIV) in the presence of a coupling agent such as N,N'-carbonyldiimidazole as described previously.

Compounds of formula (V) where $R^3$, $R^4$, $R^5$ and $R^{10}$ are hydrogen atoms may be prepared from compounds of formula $R^{14}R^2C$=CH—$Y^1$ (XVI) (where $R^{14}$ is a group reducible to amino, e.g. nitro) by reduction using a reducing agent such as a complex metal hydride e.g. lithium aluminium hydride and using the reaction conditions described in general process (1).

Compounds of formula (XVI) where $R^{14}$ is a nitro group may be prepared from compounds of formula $Y^1CHO$ (XVII) by condensation with the appropriate alkyl nitro compound in the presence of a base such as ammonium acetate.

Compounds of formula (XVII) where $Y^1$ is substituted in the 2-position by an alkyl group can be prepared from a compound of formula (XVIII)

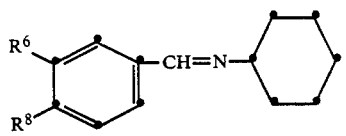

(where $R^6$ and $R^8$ are as defined in formula (I) or, when $R^6$ and/or $R^8$ are hydroxy, a protected form thereof) by introduction of the alkyl group using a strong base such a n-butyl lithium, and the appropriate haloalkane followed by hydrolysis under acid conditions.

Compounds of formula (V) (where $R^2$ and $R^3$ are methyl or ethyl groups) and $R^4$ and $R^5$ are hydrogen atoms may be prepared from compounds of formula $R^{15}O_2CNHCR^2R^3CH_2Y^1$ (XIX) (where $R^{15}$ is a protecting group such as a benzyl group) by removal of the protecting group for example by catalytic hydrogenolysis.

Compounds of formula (XIX) may be prepared from compounds of formula $HO_2CCR^2R^3CH_2Y^1$ (XX) by means of a Curtius rearrangement followed by solvolysis of the isocyanate thus formed with an alcohol such as benzyl alcohol. The Curtius rearrangement is carried out by treating a reactive derivative of a compound of formula (XX), such as an activated ester formed with ethylchloroformate, with an azide, e.g. sodium azide, and heating for example to about 100° C. in toluene.

Compounds of formula (XX) may be prepared from compounds of formula $R^{16}O_2C(CH_2)_2Y^1$ (XXI) (where $R^{16}$ is a protecting group as defined previously) by alkylation using a strong base, such as n-butyl lithium, and a haloalkane, such as iodomethane or iodoethane, followed by removal of the protecting group as described previously.

Compounds of formula (XXI) may be prepared by reduction of compounds of formula $HO_2CCH$=$CHY^1$ (XXII) by catalytic hydrogenation as described previously, followed by esterification to yield the protected derivative.

Compounds of formula (XXII) may be prepared from compounds of formula (XVII) using the Knoevenagel reaction i.e. by condensing with malonic acid in the presence of a base such as piperidine and/or pyridine.

Compounds of formulae (IV), (IX), (X), (XI), (XII), (XIII), (XIV), (XV), (XVIII) and the alkylating agents LXL and $OHCX^1CHO$ are either known compounds or may be prepared by conventional methods from known starting materials. Suitable methods are described in the exemplification included hereinafter.

Compounds of formula (VI) may be prepared by processes (1) and (2).

The following examples illustrate the invention. Temperatures are in °C. Solutions were dried using magnesium sulphate or sodium sulphate. Thin layer chromatography (t.l.c.) was carried out on silica plates. FCC - Flash Column Chromatography was carried out on silica (Merck 9385).

The following abbreviations are used: THF - tetrahydrofuran; Pd-C Palladium on carbon; PdO-C Palladium Oxide on carbon.

Intermediate 1 is 2-Ethyl-3,4-dimethoxybenzeneacetonitrile.

Intermediate 2 is 2-Ethyl-3,4-dimethoxybenzeneethanamine hydrochloride.

Intermediate 3

2-Ethyl-3,4-bis(phenylmethoxy)benzeneethanamine hydrochloride

Intermediate 7 (10 g) in dry THF (56 ml) was added to borane-THF complex (1M in THF, 84 ml) over 5 min at 0°, and was then heated at reflux for 6 h under nitrogen. The mixture was cooled, quenched with methanol (25 ml), and then heated at reflux for 30 min, cooled, acidified with 2N hydrochloric acid and reheated at 60° for 1 h. The mixture was treated with ethyl acetate (250 ml), and the organic layer extracted with water. The aqueous extract was basified and extracted with ethyl acetate. The extracts were dried, filtered and evaporated to give an oil (6 g) which was dissolved in ethereal methanol and treated with ethereal hydrogen chloride to give the title compound as white needles, m.p. 155°–165°.

Intermediate 4

2,2,2-Trifluoro-N-[2-(2-ethyl-3,4-dimethoxyphenyl)ethyl]acetamide

Triethylamine (22.3 ml) was added to Intermediate 2 (17.0 g) in dry dichloromethane (120 ml), under nitrogen. The solution was ice-bath cooled. Trifluoroacetic anhydride (22.6 ml) in dry dichloromethane (80 ml) was added dropwise over 1 h. The solution was stirred for 2 h, washed successively with 2N hydrochloric acid, 8% sodium bicarbonate and brine, dried and concentrated in vacuo. The resultant oil was purified by FCC, using ether/hexane (1:1) as eluent to give the title compound as an off-white solid (18.1 g), m.p. 80°–81°.

Intermediate 5

2-Ethyl-3,4-dimethoxybenzeneacetic acid

A solution of Intermediate 1 (0.93 g) and sodium hydroxide (6 g) in ethanol (40 ml) and water (20 ml) was heated at reflux for 24 h. The solution was evaporated in vacuo, acidified with 2N hydrochloric acid and extracted with ether. The extracts were washed with water, dried and evaporated. The residue was purified by FCC using ether/hexane (1:1) as eluent to give the title compound as white crystals (0.75 g), m.p. 89°–90°.

Intermediate 6

2-Methyl-3,4-dimethoxybenzeneacetic acid (6.6 g) m.p. 102°–104° was prepared from 2-methyl-3,4-dimethoxybenzeneacetonitrile (16 g) according to the method of Intermediate 5.

Intermediate 7

2-Ethyl-3,4-bis(phenylmethoxy)benzeneacetonitrile (i) 2-Ethyl-3,4-dihydroxybenzeneacetonitrile A solution of boron tribromide in dichloromethane (1M; 30 ml) was added cautiously with water-bath cooling to a solution of Intermediate 1 (2.05 g) in dry dichloromethane (15 ml). The resultant solution was stood at room temperature for 2.5 h, and quenched with ice. After a further 15 min the mixture was diluted with ether. The organic phase was separated, washed with brine, dried and evaporated. The oil obtained was dissolved in ether/cyclohexane (1:2, 250 ml) and filtered through hyflo. The filtrate was concentrated in vacuo to 100 ml and the supernatent liquors were decanted from a solid which was then dried to give the title compound (1.68 g) m.p. 101°–103°.

(ii) 2-Ethyl-3,4-bis(phenylmethoxy)benzeneacetonitrile

Solid potassium carbonate (1.94 g) was added at room temperature to a solution of the product from stage (i) (1 g) in dry dimethylformamide. Benzyl bromide (2.41 g) was added. The mixture was stirred overnight. Ice and water were added. The mixture was extracted with ether. The extracts were washed with water, dried and evaporated. The oil obtained was purified by FCC using ether/hexane (1:1) as eluent, to give the title compound as a yellow oil which crystallised slowly (1.82 g) m.p. 44°–47.5°.

Intermediate 8

1,6-Dibromo-3-hexyne

A solution of carbon tetrabromide (16.7 g) in methylene chloride (70 ml) was added to a solution of 3-hexyne-1,6-diol (2.5 g) in methylene chloride (125 ml). The solution was cooled to 0°, and a solution of triphenylphosphine (13.2 g) in methylene chloride (70 ml) was then added dropwise over 0.25 h. The solution was stirred at 0° for 1 h, and then warmed to 21°. The dichloromethane was removed in vacuo and the residue was triturated with ether (300 ml). The resultant suspension was filtered, and evaporated to give an oil which was purified by FCC using hexane as eluent followed by hexane/ether (4:1) to give the title compound (4.64 g) as a colourless oil. T.l.c. (hexane:ether 7:1) Rf 0.65.

Intermediate 9

N-[2-(4-aminophenyl)ethyl]-1,3-dihydro-1,3-dioxo-2H-isoindolehexanamide

A solution of 6-[1,3-dihydro-1,3-dioxo-2H-isoindolyl]hexanoic acid (1.31 g) and p-aminophenethylamine (0.77 g) in dry dichloromethane (25 ml) at 5° was treated with diphenylphosphorylazide (1.62 ml) followed by triethylamine (1.05 ml). The resultant solution was stood at room temperature for 19 h. The mixture was treated with 2N sodium hydroxide (50 ml) and extracted with dichloromethane. The extracts were dried and concentrated in vacuo to a semi-solid, which was purified by FCC using ethyl acetate as eluent to give the title compound as a pale yellow solid (1.32 g), m.p. 124°–126°.

In a similar manner were prepared Intermediates 10–17.

Intermediate 10

3,3'-Oxybis[N-[2-[2-ethyl-3,4-bis(phenylmethoxy)phenyl]ethyl]propanamide (9.31 g), m.p. 159°–160° from Intermediate 3 (18.1 g) and 3,3'-oxydipropanoic acid (4.05 g).

Intermediate 11

N,N'-Bis[2-[2-ethyl-3,4-bis(phenylmethoxy)phenyl]ethyl]-4-oxoheptanediamide (6.93 g), m.p. 188°–192° from Intermediate 3 (9.39 g) and 4-oxoheptanedioic acid (2.26 g).

Intermediate 12

N,N'-Bis-[2-(2-ethyl-3,4-dimethoxyphenyl)ethyl]-3-methylhexanediamide (1.1 g), m.p. 152°–153° from Intermediate 2 (1 g) and 3-methylhexanedioic acid (0.38 g).

Intermediate 13

N-[6-[[2-(4-Aminophenyl)ethyl]amino]-6-oxohexyl]-2-ethyl-3,4-dimethoxybenzeneacetamide (1.73 g) m.p. 202°–205° from Intermediate 5 (1.38 g) and Intermediate 23 (1.53 g).

Intermediate 14

2-Ethyl-3,4-dimethoxy-N-[6-[[(4-nitrophenyl)acetyl]amino]hexyl]benzeneacetamide (7.7 g), m.p. 146°–148° from Intermediate 18 (9.5 g) and 4-nitrophenylacetic acid (5.8 g).

Intermediate 15

3,3'-Thiobis[N-[2-[2-ethyl-3,4-bis(phenylmethoxy)phenyl]ethyl]propanamide (2.17 g), m.p. 115°–117° from Intermediate 2 (2.0 g) and 3,3'-thiodipropionic acid (0.89 g).

Intermediate 16

3,3'-Sulphonylbis[N-[2-[2-ethyl-3,4-bis(phenylmethoxy)phenyl]ethyl]propanamide (1.2 g), m.p. 164°–166° from Intermediate 2 (1 g) and 3,3'-sulphonyldipropionic acid (0.5 g).

Intermediate 17

N,N'-Bis[2-(2-ethyl-3,4-dimethoxyphenyl)ethyl]pentanediamide (3.0 g), m.p. 171°–173° from Intermediate 2 (3.00 g) and glutaric acid (0.95 g).

Intermediate 18

N-(6-Aminohexyl)-2-ethyl-3,4-dimethoxybenzeneacetamide

Carbonyldiimidazole (15 g) was added to a solution of Intermediate 5 (20 g) in dry dichloromethane at 0° under nitrogen. The mixture was stirred at room temperature for 2 h and then added dropwise to a solution of 1,6-hexanediamine (50 g) in dichloromethane (500 ml) at 0°. The resultant solution was stirred at room temperature for 24 h and then concentrated in vacuo. The residue was acidified (2N hydrochloric acid) and washed with ether. The aqueous layer was basified (2N sodium hydroxide) and extracted with dichloromethane. The extracts were washed with water, dried and concentrated in vacuo to give a white waxy solid. Recrystallization from methanol/ethyl acetate gave the title compound as a white powder (26 g), m.p. 136°–138°.

Intermediate 19

N,N'-(1,6-Hexanediyl)bis[u,4-dimethoxy-2-methylbenzeneacetamide]

(5 g) m.p. 176°–178° was prepared from Intermediate 6 (6.5 g) and 1,6-hexanediamine (1.74 g) in a mixture of dichloromethane and dimethylformamide (1:1), following the method of Intermediate 18.

Intermediate 20

4-Ethyl-1,3-benzodioxole-5-carboxaldehyde n-Butyl lithium in hexane (1.6M, 320 ml) was added under nitrogen to a stirred solution of N-(1,3-benzodioxol-5-ylmethylene)cyclohexanamine (100 g) in dry THF (500 ml) at −78°. After 15 min ethyl iodide (50 ml) was added and the mixture was allowed to warm slowly to −50°. Water was then added and the mixture was extracted with ether. The extracts were concentrated in vacuo and the concentrate heated in 2N hydrochloric acid (250 ml) on a steam bath for 20 min. The resultant solution was diluted with water and extracted with ether. The extracts were dried and evaporated to give the title compound (38 g) as a pale yellow oil. T.l.c. (ether:hexane, 1:9) Rf 0.3.

Intermediate 21

N-[6-[[(3,4-Dimethoxy-2-methylphenyl)acetyl]amino]hexyl](2-ethyl-3,4-dimethoxy)benzeneacetamide Carbonyldiimidazole (0.54 g) was added portionwise to a stirred cooled solution of Intermediate 6 (0.68 g) in dichloromethane (20 ml). Nitrogen was bubbled through the mixture, which was stirred at room temperature for 15 h. Intermediate 18 (1 g) in dry dichloromethane (25 ml) was added dropwise to the cooled solution. The mixture was stirred at room temperature for 24 h. The solution was concentrated in vacuo. The solid obtained was recrystallised from methanol to give the title compound as a white solid (1 g), m.p. 164°–166°.

Intermediate 22

2-Ethyl-3,4-dimethoxy-N-[6-[[(4-methoxyphenyl)acetyl]amino]hexyl]benzeneacetamide (1 g), m.p. 123°–125° was prepared from Intermediate 18 (0.9 g) and 4-methoxybenzeneacetic acid (0.5 g), according to the method of Intermediate 21.

Intermediate 23

6-Amino-N-[2-(4-aminophenyl)ethyl]hexanamide fumarate

A stirred suspension of Intermediate 9 (21.5 g) in ethanol (450 ml) was treated with hydrazine hydrate (11.0 ml). The mixture was heated at reflux for 30 min to give a paste. The solvent was removed in vacuo. The residue was heated at reflux in 2N hydrochloric acid (550 ml) and cooled to room temperature. The resultant suspension was filtered. The filtrate was washed with ethyl acetate, basified, saturated with sodium chloride and extracted with dichloromethane. The extracts were dried and concentrated in vacuo to give a yellow oil. A portion of this oil (4.47 g) was dissolved in methanol and treated with fumaric acid (2.08 g). The resultant solution was concentrated in vacuo and the residue was crystallised from methanol/ethyl acetate to give the title compound as a light brown solid (5.97 g), m.p. 168°–172°.

Intermediate 24

2-Ethyl-3,4-dimethoxy-N-[6-[[2-[4-[(methylsulphonyl)amino]phenyl]ethyl]amino]-6-oxohexyl]benzeneacetamide A suspension of Intermediate 13 (5.83 g) in dry pyridine (115 ml) was treated with methanesulphonylchloride (1.98 ml). The resultant suspension was stirred at room temperature for 24 h and concentrated in vacuo to produce a paste. This material was washed with water (500 ml) and purified by FCC, using ethyl acetate/methanol (20:1) as eluent. The solid obtained was crystallised from ethyl acetate to give the title compound as a white solid (3.96 g), m.p. 110°–112°.

Intermediate 25

N-(6-Bromohexyl)-N-[2-(2-ethyl-3,4-dimethoxyphenyl)ethyl]-2,2,2-trifluoroacetamide Sodium hydride (50% dispersion in oil, 0.72 g) was stirred in hexane for 30 min, under nitrogen. The hexane was replaced with dry dimethylformamide (25 ml) and a solution of Intermediate 4 (5 g) in dry dimethylformamide (25 ml) was added. The reaction mixture was stirred at room temperature for 45 min and cooled. 1,6-Dibromohexane (21.9 g) was added and the mixture was heated at 80° for 2 h. The reaction mixture was poured onto a mixture of ice and dilute hydrochloric acid and extracted with ether. The extracts were washed with water, dried and concentrated in vacuo. Excess dibromohexane was removed by distillation (0.1 mmHg 100°–105°) to give the title compound as a pale orange oil (8 g).

Analysis Found: C, 50.7; H, 6.4; N, 3.2. $C_{20}H_{29}F_3BrNO_3$ requires: C, 51.3; H, 6.2; N, 3.0%.

Intermediate 26

N,N'-(1,7-Heptanediyl)bis[N-[2-(2-ethyl-3,4-dimethoxyphenyl)ethyl]-2,2,2-trifluoroacetamide]

(2.3 g). T.l.c. (ether:hexane, 1:1) Rf 0.3 was prepared from Intermediate 4 (3 g) and 1,7-dibromoheptane (1.16 g), according to the method of Intermediate 25.

Intermediate 27

N,N'-(1,6-Hexanediyl)bis[2-ethyl-3,4-dimethoxybenzeneacetamide]

A mixture of Intermediate 5 (8.6 g), thionyl chloride (18 ml) and dichloromethane (480 ml) was refluxed for 2 h and evaporated in vacuo to give a solid. A stirred suspension of the solid (15 g), 1,6-diaminohexane (3.6 g) and anhydrous potassium carbonate (8 g) in dry dichloromethane (400 ml) was heated at reflux for 24 h. The solvent was evaporated, water was added and the mixture was extracted with chloroform. The extracts were dried and evaporated to give a solid which was triturated with a mixture of ether and hexane to give the title compound (5.5 g) as a cream solid, m.p. 169°–172°.

Intermediate 28

3-(4-Ethyl-1,3-benzodioxol-5-yl)-2-propenoic acid

A mixture of Intermediate 20 (35 g), malonic acid (41 g), piperidine (15 ml) and dry pyridine (350 ml) was heated at reflux for 4 h, cooled and poured into a mixture of 2N hydrochloric acid and ice. The resulting solid was collected, washed with water, dried, and recrystallised from ethyl acetate to give the title compound (17 g), m.p. 204°–204.5°.

Intermediate 29

4-Ethyl-α,α-dimethyl-1,3-benzodioxole-5-ethanamine hydrochloride (i) 4-Ethyl-1,3-benzodioxole-5-propanoic acid A suspension of Intermediate 28 (21.7 g) in methanol (600 ml) was stirred over Pd-C under a hydrogen atmosphere until hydrogen uptake ceased. The catalyst was filtered off and the filtrate evaporated. The resultant white solid was crystallised from ethyl acetate to give the title compound (20 g), m.p. 127°–128°.

(ii) Methyl 4-ethyl-1,3-benzodioxole-5-propanoate

A solution of the product from Stage (i) (20 g) in methanol (400 ml) and concentrated sulphuric acid (40 ml) was heated on a steam bath for 20 min, cooled and poured onto a mixture of ice and water. The mixture was extracted with ether and the extracts were dried and evaporated. The residue was purified by FCC using hexane/ether (7:3) as eluent to give the title compound (19.2 g), m.p. 44°–46°.

(iii) Methyl 4-ethyl-α,α-dimethyl-1,3-benzodioxole-5-propanoate n-Butyl lithium in hexane (1.55M, 44 ml) was added to a stirred solution of diisopropylamine (6.85 g) in dry THF (200 ml) at 0° under nitrogen. The solution was cooled to −78° and a solution of the product from Stage (ii) (16 g) in dry THF (200 ml) was added over 30 min. After a further 45 min methyl iodide (5.1 ml) in hexamethylphosphoramide (11.7 ml) was added and the reaction was allowed to warm to room temperature. The reaction was quenched with saturated aqueous ammonium chloride (1 l) and extracted with ether. The extracts were washed with water, dried and evaporated. The residue was submitted twice more to the above methylation conditions using appropriately reduced quantities of reagent. Distillation of the final residue in vacuo gave the title compound (10.2 g), b.p. 150–155/0.1 Torr.

(iv) 4-Ethyl-α,α-dimethyl-1,3-benzodioxole-5-propanoic acid

A solution of the product from Stage (iii) (10 g) and 2N sodium hydroxide (50 ml) in ethanol (50 ml) was heated under reflux for 30 min. The solution was cooled, poured into water, acidified with 2N hydrochloric acid and extracted with ether. The extracts were dried and evaporated and the residue purified by FCC using hexane/ether (7:3) as eluent. The product was crystallised from hexane to give the title compound (4.2 g) as a white solid, m.p. 73°–74°.

(v) Phenylmethyl [2-(4-ethyl-1,3-benzodioxol-5-yl)-1,1-dimethylethyl]carbamate

Ethyl chloroformate (1.87 g) in acetone (10 ml) was added to a stirred solution of the product from Stage (iv) (3.6 g) and triethylamine (1.58 g) in acetone (40 ml) and water (5 ml) at 5°. A solution of sodium azide (1.22 g) in water (10 ml) was added and the mixture was stirred for 30 min at 5°. The mixture was diluted with water and extracted with toluene. The extracts were dried, heated on a steam bath for 1 h and evaporated. The residue was heated in benzyl alcohol (21 ml) at 100° for 18 h. The mixture was then distilled in vacuo and purified by FCC using hexane/ether (7:3) as eluent to give the title compound as a colourless oil (4 g).

N.m.r. (CDCl$_3$) δ7.36(s, 5H); 6.5(ab, 2H); 5.89(s, 2H); 5.08(s, 2H); 4.59(br.s, 1H); 2.95(s, 2H); 2.65(q, 2H); 1.3(s, 6H); 1.12(t, 3H).

(vi) 4-Ethyl-α,α-dimethyl-1,3-benzodioxole-5-ethanamine hydrochloride

A solution of the product from Stage (v) (0.5 g) in ethanol (25 ml) was hydrogenated over 10% Pd-C. After 1.5 h the catalyst was filtered off and the filtrate evaporated. The residue was treated with ethereal hydrogen chloride to give a white solid which was crystallised from methanol/ethyl acetate to give the title compound (0.14 g), m.p. >300°. T.l.c. (toluene:ethanol:ammonia, 78:20:2) Rf 0.52.

Intermediate 30

6-[[2-(2-Ethyl-3,4-dimethoxyphenyl)ethyl]amino]-6-oxohexanoic acid (i) Methyl 6-[[2-(2-ethyl-3,4-dimethoxyphenyl)ethyl]amino]-6-oxohexanoate A solution of 6-chloro-6-oxohexanoic acid methyl ester (10 g) in dry dichloromethane (100 ml) was added dropwise to a stirred, cooled solution of Intermediate 2 (10.4 g) and triethylamine (5.65 g) in dry dichloromethane (100 ml). The reaction mixture was stirred for 1 h at room temperature, the solvent was removed in vacuo and the residue was purified by FCC using ether as eluent to give the title compound (15 g) as a white solid, m.p. 37°-39°.

(ii) 6-[[2-(2-Ethyl-3,4-dimethoxyphenyl)ethyl]amino]-6-oxohexanoic acid

A mixture of the product from Stage (i) (11 g), 2N sodium hydroxide solution (200 ml) and ethanol (300 ml) was heated under reflux for 1 h. The solution was cooled and poured into water (1000 ml). The mixture was washed with ether, acidified with 2N hydrochloric acid and then extracted with ether. The extracts were washed with water, dried and evaporated to give the title compound (8.4 g) as a white solid, m.p. 92°-94°.

Intermediate 31

N-[2-(4-Ethyl-1,3-benzodioxol-5-yl)-1,1-dimethylethyl]-N'-[2-(2-ethyl-3,4-dimethoxyphenyl)ethyl]hexanediamide Ethyl chloroformate (0.74 g) was added to a stirred solution of Intermediate 30 (2.17 g) and triethylamine (1.01 g) in dry dichloromethane (80 ml) at 0°-5°. The reaction mixture was stirred for 10 min, and a solution of Intermediate 29 (1.5 g) in dry dichloromethane (20 ml) was then added dropwise over 10 min. After a further 20 min, the solution was washed with 8% sodium bicarbonate solution, followed by 2N hydrochloric acid. The solution was dried and evaporated to dryness. The residue was purified by FCC using ethyl acetate as the eluent to give the title compound (1.4 g) as a white solid, m.p. 103°-104.5°.

Intermediate 32

N,N'-Bis-[2-(2-chloro-3,4-dimethoxyphenyl)ethyl]hexanediamide

A mixture of 2-chloro-3,4-dimethoxybenzeneethanamine (2 g), adipoyl chloride (0.85 g) and triethylamine (1.3 ml) was stirred in dry acetonitrile (40 ml) at room temperature for 1 h. The solvent was removed in vacuo and the residual white solid was stirred with water for 30 min, collected and dried in vacuo at 90° to give the title compound (2 g), m.p. 159°-161°.

Intermediate 33

Methyl 5-[2-[[6-[[2-(2-ethyl-3,4-dimethoxyphenyl)ethyl](trifluoroacetyl)amino]hexyl](trifluoroacetyl)amino]ethyl]-2-methoxybenzoate (i) Methyl 2-methoxy-5-[2-[(trifluoroacetyl)amino]ethyl]benzoate A solution of methyl-5-cyanomethyl-2-methoxy benzoate (6 g) in methanol (240 ml) was hydrogenated over pre-reduced Adams catalyst (0.4 g) in the presence of ethanolic hydrogen chloride (27 ml). The catalyst was removed by filtration and the filtrate was concentrated in vacuo. The oil and trifluoroacetic anhydride (25 ml) in dry dichloromethane (25 ml) were stirred at room temperature for 18 h. The mixture was quenched with methanol at 0° and concentrated in vacuo to give a solid. Purification by FCC using ether/hexane (1:3) as eluent gave the title compound as a white solid (6.8 g), m.p. 61°-63°.

(ii) Methyl 5-[2-[[6-[[2-(2-ethyl-3,4-dimethoxyphenyl)ethyl](trifluoroacetyl)amino]hexyl](trifluoroacetyl)amino]ethyl]-2-methoxybenzoate A suspension of sodium hydride (50% dispersion in oil, 0.2 g) in hexane was stirred at 21° for 30 min under nitrogen. The hexane was removed and replaced with dry dimethylformamide (5 ml). A solution of the product from Stage (i) (1.3 g) in dry dimethylformamide (15 ml) was added dropwise to the reaction mixture which was stirred at 21° for 1 h. The solution was cooled to 0° and treated with a solution of Intermediate 25 (5 g) in dry dimethylformamide (5 ml). The reaction mixture was then heated at reflux for 18 h before being poured onto ice-water. 2N Hydrochloric acid was then added and the mixture extracted with ether. The extracts were washed with water, dried and concentrated in vacuo. The resultant oil was purified twice by FCC using ether/hexane (1:2) as eluent for the first procedure and ethyl acetate/hexane (1:1) for the second. The title compound was obtained as a colourless oil (1.4 g).

Analysis Found: C, 57.2; H, 6.4; N, 4.0. $C_{33}H_{42}F_6N_2O_7$ requires: C, 57.2; H, 6.1; N, 4.0%.

EXAMPLE 1

4,4'-[Thiobis[(3,1-propanediylimino)-2,1-ethanediyl]]bis[3-ethyl-1,2-benzenediol]dihydrobromide dihydrate (i) N,N'-[Thiobis(3,1-propanediyl)]bis[2-ethyl-3,4-dimethoxybenzeneethanamine]dihydrochloride Borane-THF complex (1M in THF; 30 ml) was added to a solution of Intermediate 15 (2.11 g) in dry THF (150 ml) at 21° under nitrogen. The mixture was stirred and heated at reflux under nitrogen for 21 h, cooled and evaporated. 2N hydrochloric acid was added to the residue, and the mixture was stirred and heated at 100° for 3.5 h. It was then cooled and basified with 2N sodium hydroxide. The mixture was extracted with dichloromethane and ethyl acetate. The combined extracts were washed with saturated brine, dried and evaporated to give a viscous oil which was dissolved in methanol. Ethereal hydrogen chloride was added. The solvents were evaporated and the residual solid was recrystallised from a mixture of methanol, ethyl acetate and hexane to give the title compound (0.97 g) as a white powder, m.p. 184°–186°.

(ii)

4,4'-[Thiobis[(3,1-propanediylimino)-2,1-ethanediyl]-]bis[3-ethyl-1,2-benzenediol]dihydrobromide dihydrate A solution of the product from Stage (i) (400 mg) in methanol (5 ml) and water (5 ml) was basified with 2N sodium carbonate. The mixture was extracted with ethyl acetate and the extracts were evaporated to give an oil which was dissolved in dichloromethane (50 ml). A solution of boron tribromide in dichloromethane (1M; 5.0 ml) was added dropwise to the vigorously stirred solution. The resulting mixture was stirred at 21° under nitrogen for 18 h and then cooled to 0°. Methanol was added and, the resulting solution was heated under reflux for 0.75 h, cooled and evaporated. The solid obtained was dissolved in absolute ethanol and hexane was added dropwise to the vigorously stirred solution until a gum precipitated. The solvents were decanted and the residue was dried in vacuo to give the title compound (344 mg) as a white foam.

Analysis Found: C, 46.1; H, 6.3; N, 3.9. $C_{26}H_{40}N_2O_4S.2HBr.2H_2O$ requires: C, 46.3; H, 6.8; N, 4.2%.

EXAMPLE 2

4,4'-[Sulphonylbis[(3,1-propanediylimino)-2,1-ethanediyl]]bis[3-ethyl-1,2-benzenediol]dihydrobromide sesquihydrate (i)

N,N'-[Sulphonylbis(3,1-propanediyl)]bis[2-ethyl-3,4-dimethoxybenzeneethanamine]dihydrochloride Borane-THF complex (1M; 6 ml) was added to a solution of Intermediate 16 (0.6 g) in dry THF (50 ml) at 0° under nitrogen. The solution was stirred and heated under reflux for 18 h, cooled and concentrated in vacuo. 2N hydrochloric acid was added to the residue and the mixture was stirred and heated at 100° for 1 h. On cooling, a white solid precipitated which was collected and dried in vacuo to give the title compound as a white powder (0.4 g), m.p. 212°–215°.

(ii)

4,4'-[Sulphonylbis[(3,1-propanediylimino)-2,1-ethanediyl]]bis[3-ethyl-1,2-benzenediol]dihydrobromide sesquihydrate Boron tribromide (1M; 9 ml) was added to a stirred suspension of product from Stage (i) (0.6 g) in dry dichloromethane (90 ml). The mixture was stirred at 21° for 24 h under nitrogen. The cloudy mixture was cooled to 0° and treated cautiously with methanol. The solution was heated at reflux for 1 h, cooled and concentrated in vacuo to give the title compound as a pale pink solid (0.6 g), m.p. 130°–133°, softens 90°.

Analysis Found: C, 44.5; H, 6.1; N, 3.8. $C_{26}H_{40}N_2O_6S.2HBr1.5H_2O$ requires: C, 44.8; H, 6.4; N, 4.0%.

EXAMPLE 3

4-[2-[[6-[[2-(3,4-Dihydroxy-2-methylphenyl)ethyl-]amino]hexyl]amino]ethyl]-3-ethyl-1,2-benzenediol dihydrobromide (i)

N-[2-(3,4-Dimethoxy-2-methylphenyl)ethyl]-N'-[2-(2-ethyl-3,4-dimethoxyphenyl)ethyl]-1,6-hexanediamine dihydrochloride Borane-THF complex (6 ml, 1M) was added dropwise to a stirred solution of Intermediate 21 (500 mg) in dry THF (30 ml), at ice bath temperature, under nitrogen. The mixture was refluxed for 20 h and methanol was added to the cooled solution, which was then evaporated in vacuo. The residue was heated in 2N hydrochloric acid at reflux for 4 h. The solution was cooled and the solid which precipitated was collected and dried to give the title compound as a white powder (300 mg), m.p. 263° (dec).

(ii)

4-[2-[[6-[[2-(3,4-Dihydroxy-2-methylphenyl)ethyl-]amino]hexyl]amino]ethyl]-3-ethyl-1,2-benzenediol dihydrobromide A solution of boron tribromide (1.2 ml) in dichloromethane (10 ml) was added dropwise under nitrogen to a stirred, cooled solution of the product from Stage (i) (1.2 g) in dry dichloromethane (100 ml) at 0°. The mixture was stirred at room temperature for 5 h and methanol was then added. The mixture was evaporated in vacuo to give a solid which was recrystallised from methanol/ethyl acetate to give the title compound as a white powder (1 g), m.p. 178°–180°.

Analysis Found: C, 50.5; H, 6.6; N, 4.4; $C_{25}H_{38}N_2O_4.2HBr$ requires: C, 50.7; H, 6.8; N, 4.7%.

EXAMPLE 4

4,4'-[1,6-Hexanediylbis(imino-2,1-ethanediyl)]bis[3-ethyl-1,2-benzenediol]dihydrobromide (i)

N,N'-Bis[2-(2-ethyl-(3,4-dimethoxyphenyl)ethyl]-1,6-hexanediamine dihydrochloride A suspension of Intermediate 27 (5.2 g) in dry THF (220 ml) was cooled to 0° and 1M borane-THF complex (65 ml) was added under nitrogen. The mixture was heated at reflux for 5 h. The solution was cooled, treated with methanol and evaporated in vacuo. The residue in 2N hydrochloric acid was heated for 20 h and then cooled. A white solid precipitated which was collected and dried to give the title compound (2.78 g), m.p. 223°–225°.

(ii)

4,4'-[1,6-Hexanediylbis(imino-2,1-ethanediyl)]bis[3-ethyl-1,2-benzenediol]dihydrobromide Boron tribromide (0.87 g) was added dropwise to a solution of the product from Stage (i) (1 g) in dry dichloromethane (70 ml) at 0° under nitrogen. The mixture was then stirred at room temperature for 18 h, cooled to 5° and treated dropwise with methanol. The solution was heated at reflux for 1 h and evaporated in vacuo to give a solid which was recrystallised from methanol/ethyl acetate to give the title compound as a white solid (0.75 g), m.p. 205°–207°.

Analysis Found: C, 52.0; H, 7.1; N, 4.4. $C_{26}H_{40}N_2O_4.2HBr$ requires: C, 51.5; H, 7.0; N, 4.6%.

In a similar manner were prepared Examples 5–9.

EXAMPLE 5

(i)

N,N'-Bis[2-(2-ethyl-3,4-dimethoxyphenyl)ethyl]-3-methylhexane-1,6-diamine dihydrochloride (0.90 g), m.p. 198°–200°.
From Intermediate 12 (0.90 g).

(ii)

4,4'-[(3-Methyl-1,6-hexanediyl)bis(imino-2,1-ethanediyl)]bis[3-ethyl-1,2-benzenediol]dihydrobromide hydrate (0.81 g), m.p. 135°–138°.
Analysis Found: C, 50.4; H, 7.0; N, 4.2; Br, 25.2. $C_{27}H_{42}N_2O_4.2HBr.H_2O$ requires: C, 50.7; H, 7.2; N, 4.3; Br, 25.5%.
From Example 5(i) (0.8 g).

EXAMPLE 6

(i)

N-[2-(2-Ethyl-3,4-dimethoxyphenyl)ethyl]-N'-[2-(4-methoxyphenyl)ethyl]-1,6-hexanediamine dihydrochloride (350 mg), m.p. 263°. From Intermediate 22 (500 mg)

(ii)

3-Ethyl-4-[2-[[6-[[2-(4-hydroxyphenyl)ethyl]amino]hexyl]amino]ethyl]-1,2-benzenediol dihydrobromide (2.2 g), m.p. 191°–193°.
Analysis Found: C, 51.3; H, 6.8; N, 4.7. $C_{24}H_{36}N_2O_3.2HBr$ requires: C, 51.3; H, 6.8; N, 5.0%.
From Example 6(i) (2 g).

EXAMPLE 7

(i)

N-[2-(2-Ethyl-3,4-dimethoxyphenyl)ethyl]-N'-[2-(4-nitrophenyl)ethyl]-1,6-hexanediamine dihydrochloride (783 mg), m.p. 230°–233°.
From Intermediate 14 (1.3 g).

(ii)

3-Ethyl-4-[2-[[6-[[2-(4-nitrophenyl)ethyl]amino]hexyl]amino]ethyl]-1,2-benzenediol dihydrobromide hydrate (563 mg), m.p. 147°–150°.
Analysis Found: C, 47.9; H, 6.2; N, 6.7. $C_{24}H_{35}N_3O_4.2HBr.\frac{3}{8}H_2O$ requires: C, 47.8; H, 6.3; N, 7.0%.
From Example 7(i) (500 mg).

EXAMPLE 8

(i)

N-[4-[2-[[6-[[2-(2-Ethyl-3,4-dimethoxyphenyl)ethyl]amino]hexyl]amino]ethyl]phenyl]methanesulphonamide dihydrochloride (2.75 g), m.p. 238°–241°. From Intermediate 24 (3.4 g).

(ii)

N-[4-[2-[[6-[[2-(2-Ethyl-3,4-dihydroxyphenyl)ethyl]amino]hexyl]amino]ethyl]phenyl]methanesulphonamide dihydrobromide hydrate (2.73 g), m.p. 165°–169° (dec).
Analysis Found: C, 45.2; H, 6.5; N, 6.2. $C_{25}H_{39}N_3O_4S.2HBr.H_2O$ requires: C, 45.7; H, 6.3; N, 6.4%.

From Example 8(i) (2.4 g).

EXAMPLE 9

(i)

N,N'-Bis[2-(2-ethyl-3,4-dimethoxyphenyl)ethyl]-1,5-pentanediamine dihydrochloride (2.64 g), m.p. 240°–242°. From Intermediate 17 (3.0 g).

(ii)

4,4'-[1,5-Pentanediylbis(imino-2,1-ethanediyl)]bis[3-ethyl-1,2-benzenediol]dihydrobromide hydrate (2.30 g), m.p. 145°–148°.
Analysis Found: C, 49.2; H, 6.8; N, 4.5; Br, 27.2. $C_{25}H_{38}N_2O_4.2HBr.H_2O$ requires: C, 49.2; H, 6.8; N, 4.6; Br, 26.7%.
From Example 9(i) (2.00 g).

EXAMPLE 10

4,4'-[1,6-Hexanediylbis(imino-2,1-ethanediyl)]bis[3-ethyl-1,2-benzenediol]dihydrobromide hydrate A suspension of Example 4 (i) (400 mg) in deoxygenated 48% hydrobromic acid (10 ml) was heated and stirred under reflux stirred for 24 h. A slow stream of nitrogen was passed through the mixture. The resulting solution was cooled and evaporated in vacuo. The solid obtained was recrystallised from methanol-ethyl acetate to give the title compound as a tan solid (300 mg), m.p. 200°–202°.
Analysis Found: C, 49.7; H, 6.9; N, 4.5. $C_{26}H_{40}N_2O_4.2HBr.H_2O.\frac{1}{8}EtOAc$ requires: C, 50.2; H, 6.8; N, 4.3%.

Examples 11–13 were prepared in two stages; the first stage according to the method of Example 4(i) and the second stage according to the method of Example 10.

EXAMPLE 11

(i)

N-[2-(4-Aminophenyl)ethyl]-N'-[2-(2-ethyl-3,4-dimethoxyphenyl)ethyl]-1,6-hexanediamine trihydrochloride T.l.c. (toluene:ethanol:ammonia, 78:20:2) Rf 0.4. From Intermediate 13 (2.5 g).

(ii)

4-[2-[[6-[[2-(4-Aminophenyl)ethyl]amino]hexyl]amino]ethyl]-3-ethyl-1,2-benzenediol trihydrobromide (2.04 g), m.p. 268°–270°.
Analysis Found: C, 44.5; H, 5.9; N, 6.3. $C_{24}H_{37}N_3O_2.3HBr$ requires: C, 44.9; H, 6.3; N, 6.5%.
From Example 11(i) (1.8 g).

EXAMPLE 12

(i)

N,N'-Bis[2-(2-chloro-3,4-dimethoxyphenyl)ethyl]-1,6-hexanediamine, dihydrochloride (1.18 g), m.p. 254°–256° (dec). From Intermediate 32 (1.5 g).

(ii)

4,4'-[1,6-Hexanediylbis(imino-2,1-ethanediyl)]bis[3-chloro-1,2-benzenediol]dihydrobromide (0.56 g), m.p. 194°–97°.
Analysis Found: C, 42.4; H, 5.2; N, 4.3. $C_{22}H_{30}Cl_2N_2O_4.2HBr$ requires: C, 42.7; H, 5.2; N, 4.5%.

From Example 12(i) (0.6 g).

EXAMPLE 13

(i)

N,N'-Bis[2-(3,4-dimethoxy-2-methylphenyl)ethyl]-1,6-hexanediamine dihydrochloride (3.57 g), m.p. 270°–272°. From Intermediate 19 (5 g).

(ii)

4,4'-[1,6-Hexanediylbis(imino-2,1-ethanediyl)]bis[3-methyl-1,2-benzenediol]dihydrobromide hemihydrate (3.02 g), m.p. 248°–250°.

Analysis Found: C, 48.2; H, 6.6; N, 4.5. $C_{24}H_{36}N_2O_4.2HBr.\frac{1}{2}H_2O.\frac{1}{2}MeOH$ requires: C, 48.7; H, 6.2; N, 4.6%.

From Example 13(i) (4.4 g).

EXAMPLE 14

4,4'-[Oxybis[(3,1-propanediyl(imino)-2,1-ethanediyl]]bis[3-ethyl-1,2-benzenediol]dihydrochloride hydrate (i)

N,N'-[Oxybis(3,1-propanediyl)]bis[2-ethyl-3,4-bis(phenylmethoxy)benzeneethanamine]dihydrochloride Borane-THF complex (1M in THF; 83 ml) was added to a solution of Intermediate 10 (8.30 g) in dry THF (500 ml) at 21° under nitrogen. The mixture was stirred and heated at reflux under nitrogen for 5.5 h, cooled and evaporated. 2N hydrochloric acid and THF were added to the residue, and the mixture was heated at reflux for 0.5 h and cooled. The THF was evaporated. The mixture was filtered. The solid residue was washed with water and then recrystallised from methanol/ethyl acetate/hexane to give the title compound (5.14 g) as a white powder, m.p. 192°–193°.

(ii)

4,4'-[Oxybis[(3,1-propanediylimino)-2,1-ethanediyl]]bis[3-ethyl-1,2-benzenediol]dihydrochloride hydrate A solution of the product from Stage (i) (0.66 g) in methanol (130 ml) was hydrogenated at room temperature and atmospheric pressure using pre-reduced 10% PdO-C catalyst (150 mg of wet 50% w/w material) until uptake of hydrogen was complete. The mixture was filtered and the filtrate evaporated. The resultant gum was crystallised from methanol/ethyl acetate to give the title compound (287 mg) as grey crystals, m.p. 203°–206° (dec.)

Analysis Found: C, 56.3; H, 7.6; N, 4.95. $C_{26}H_{40}N_2O_5.2HCl.H_2O$ requires: C, 56.6; H, 7.6; N, 5.1%.

EXAMPLE 15

4,4'-[4-Hydroxy-1,7-heptanediylbis(imino-2,1-ethanediyl)]bis[3-ethyl-1,2-benzenediol]dihydrochloride (i)

1,7-Bis[2-[2-ethyl-3,4-bis(phenylmethoxy)phenyl]ethyl]amino]-4-heptanol dihydrochloride (6.42 g), m.p. 168°–183° was prepared from Intermediate 14 (6.09 g) according to the method of Example 4(i) except that the crude product was triturated with boiling ether.

(ii)

4,4'-[4-Hydroxy-1,7-heptanediylbis(imino-2,1-ethanediyl)]bis[3-ethyl-1,2-benzenediol]dihydrochloride (2.43 g)

Analysis Found: C, 58.9; H, 8.3; N, 4.9; Cl, 12.7. $C_{27}H_{42}N_2O_5.2HCl$ requires: C, 59.2; H, 8.1; N, 5.1; Cl, 13.0% was obtained from the product of Stage (i) (4.00 g) according to the method of Example 14 (ii).

EXAMPLE 16

3-Ethyl-4-[2-[[6-[[2-(2-ethyl-3,4-dihydroxyphenyl)-1,1-dimethylethyl]amino]hexyl]amino]ethyl]-1,2-benzenediol dihydrobromide A suspension of Intermediate 31 (1.2 g) in dry benzene (60 ml) was added dropwise to a stirred suspension of lithium aluminium hydride (0.4 g) in dry ether (60 ml) at 0°–5° under nitrogen. The resulting mixture was then heated at reflux for 20 h. The mixture was cooled, treated with 2N sodium hydroxide solution, and extracted with ether. The extracts were washed with water, dried, and evaporated to give a pale brown oil. A sample of this oil (0.2 g) in dry ether (25 ml) was treated with ethereal hydrogen chloride to give a white solid, which was crystallized from methanol/ethyl acetate to give the title compound as white platelets (0.18 g), m.p. 223°–225°.

(ii)

3-Ethyl-4-[2-[[6-[[2-(2-ethyl-3,4-dihydroxyphenyl)ethyl]amino]hexyl]amino]-1,1-dimethylethyl]-1,2-benzenediol dihydrobromide (0.29 g), m.p. 233°–235°.

Analysis Found: C, 52.8; H, 7.4; N, 4.3. $C_{28}N_{44}N_2O_4.2HBr$ requires C, 53.0; H, 7.3; N, 4.4% was prepared from Example 16(i) (0.54 g) according to the method of Example 3(ii).

EXAMPLE 17

(E)-4,4'-[3-hexene-1,6-diylbis(imino-2,1-ethanediyl)]bis[3-ethyl-1,2-benzenediol]dihydrobromide hydrate (i)

(E)-N,N'-Bis[2-(2-ethyl-3,4-dimethoxyphenyl)ethyl]-3-hexene-1,6-diamine dihydrochloride A solution of Intermediate 2 (2.09 g) and (E)-1,6-dibromo-3-hexene (0.61 g) in absolute ethanol (18 ml) was stirred and heated at reflux for 7 h. The ethanol was evaporated. The residual gum was dissolved in methanol and excess ethereal hydrogen chloride was added. The mixture was cooled to 0° overnight. The resulting precipitate was collected and recrystallised from methanol/ethyl acetate to give the title compound (501 mg) as a white powder, m.p. 217°–219°.

(ii)

(E)-4,4'-[3-Hexene-1,6-diylbis(imino-2,1-ethanediyl)]bis[3-ethyl-1,2-benzenediol]dihydrobromide hydrate (322 mg), m.p. 202°–204° (dec).

Analysis Found: C, 50.2; H, 6.3; N, 4.3. $C_{26}H_{38}N_2O_4.2HBr.H_2O$ requires: C, 50.2; H, 6.5; N, 4.5% was obtained from the product of Stage (i) (400 mg) according to the method of Example 1(ii).

In a similar manner was prepared Example 18.

EXAMPLE 18

(i)

N,N'-Bis[2-(2-ethyl-3,4-dimethoxyphenyl)ethyl]-3-hexyne-1,6-diamine dihydrochloride (439 mg), m.p. 184°–186° (dec). From Intermediate 2 (1.67 g) and 1,6-dibromo-3-hexyne (0.48 g).

(ii)

4,4'-[3-Hexyne-1,6-diylbis(imino-2,1-ethanediyl)]bis[3-ethyl-1,2-benzenediol]dihydrobromide hemihydrate (378 mg), m.p. 130° (dec).
Analysis Found: C, 46.5; H, 5.7; N, 3.9. $C_{26}H_{36}N_2O_4.2.75HBr.0.5H_2O$ requires: C, 46.5; H, 6.0; N, 4.2%.
From Example 18(i) (425 mg).

EXAMPLE 19

(E,E)-4,4'-[2,4-Hexadiene-1,6-diylbis(imino-2,1-ethanediyl)]bis[3-ethyl-1,2-benzenediol]dihydrobromide

(i)

(E,E)-N,N'-Bis[2-(2-ethyl-3,4-dimethoxyphenyl)ethyl]-2,4-hexadiene-1,6-diamine dihydrochloride A mixture of Intermediate 2 (4.19 g) and (E,E)-2,4-hexadiene dial (1.1 g) was heated at reflux in dry benzene (250 ml) for 1 h. The solution was concentrated in vacuo. The residue in absolute ethanol (150 ml) was treated with sodium borohydride (1.51 g). The reaction mixture was stirred at room temperature for 1.5 h, diluted with water, stirred for a further 0.5 h, diluted with more water and extracted with dichloromethane. The extracts were dried and concentrated in vacuo. The oil obtained was dissolved in methanol and was treated with a slight excess of ethereal hydrogen chloride. The resultant solution was concentrated in vacuo to give a solid which was crystallised from methanol/ethyl acetate to give the title compound as an off-white solid (3.03 g), m.p. 247°–50°.

(ii)

(E,E)-4,4'-[2,4-Hexadiene-1,6-diylbis(imino-2,1-ethanediyl)]bis[3-ethyl-1,2-benzenediol]dihydrobromide (456 mg), m.p. 240°–244° (dec).
Analysis Found: C, 51.3; H, 6.1; N, 4.5. $C_{26}H_{36}N_2O_4.2HBr$ requires: C, 51.8; N, 6.4; N, 4.7% was obtained from the product of Stage (i) (1.0 g) according to the method of Example 1(ii) but replacing 2N sodium carbonate with 2N sodium hydroxide.

EXAMPLE 20

5-[2-[[6-[[2-(2-Ethyl-3,4-dihydroxyphenyl)ethyl]amino]hexyl]amino]ethyl]-2-hydroxybenzamide trihydrobromide hydrate

(i)

5-[2-[[6-[[2-(2-Ethyl-3,4-dimethoxyphenyl)ethyl]amino]hexyl]amino]ethyl]-2-methoxybenzamide A solution of Intermediate 33 (1.2 g) and ammonia (0.88N; 25 ml) in methanol (50 ml) was stirred at room temperature for 12 days. The reaction mixture was concentrated in vacuo to give the title compound as a light brown oil (1 g). I.r. (0.5% in $CHBr_3$): $NH_2$ 3490, 3380 cm$^{-1}$; amide (C=O) 1670 cm$^{-1}$.

(ii)

5-[2-[[6-[[2-(2-Ethyl-3,4-dihydroxyphenyl)ethyl]amino]hexyl]amino]ethyl]-2-hydroxybenzamide trihydrobromide hydrate (600 mg), m.p. 145°–150° (dec).
Analysis Found: C, 42.1; H, 5.8; N, 5.4. $C_{25}H_{37}N_3O_4.3HBr.H_2O$ requires: C, 42.6; H, 6.0; N, 6.0% was obtained from the product of Stage (i) (0.7 g) according to the method of Example 3(ii).

EXAMPLE 21

4,4'-[1,7-Heptanediylbis(imino-2,1-ethanediyl)]bis[3-ethyl-1,2-benzenediol]hydrobromide hydrate (2:5:2)

(i)

N,N'-Bis[2-(2-ethyl-3,4-dimethoxyphenyl)ethyl]-1,7-heptanediamine dihydrochloride A solution of Intermediate 26 (1 g) in methanol (300 ml) and 2N sodium hydroxide (50 ml) was heated on a steam bath for 1 h. After a further 18 h at 21° the solution was concentrated in vacuo and the residue was extracted with ether. The extracts were dried and concentrated in vacuo to give a oil. Ethereal hydrogen chloride was added dropwise to a solution of the oil in dry ether. The white solid which precipitated was collected and dried. Crystallization from methanol/ethyl acetate gave the title compound as a white solid (0.31 g), m.p. 233°–235°.

(ii)

4,4'-[1,7-Heptanediylbis(imino-2,1-ethanediyl)]bis[3-ethyl-1,2-benzenediol]hydrobromide hydrate (2:5:2)

(0.5 g), m.p. 182°–185°.
Analysis Found: C, 47.4; H, 6.5; N, 4.1; Br, 29.3. $C_{27}H_{42}N_2O_4.2.5HBrH_2O$ requires: C, 47.7; H, 6.5; N, 4.1; Br, 29.5% was obtained from Example 21(i) (0.45 g) according to the method of Example 3(ii).

The following are examples of suitable formulations of compounds of the invention. The term 'active ingredient' is used herein to represent a compound of the invention.

EXAMPLE A

Tablets—Direct Compression

|  | mg/tablet |
|---|---|
| Active ingredient | 50.0 |
| Microcrystalline Cellulose B.P.C. | 149.0 |
| Magnesium Stearate | 1.0 |
|  | 200.0 |

The active ingredient is sieved through a 250 μm sieve, blended with the excipients and compressed using 8.5 mm punches. Tablets of other strengths may be prepared by altering the compression weight and using punches to suit.

The tablets may be film coated with suitable film forming materials, e.g. methyl cellulose or hydroxypropylmethylcellulose using standard techniques. Alternatively the tablets may be sugar or enteric coated.

EXAMPLE B

Injection for Intravenous Administration

|  | % w/v |
|---|---|
| Active Ingredient | 1.00 |
| Water for injections B.P. to | 100.00 |

Sodium chloride may be added to adjust the tonicity of the solution and the pH may be adjusted to that of maximum stability and/or to facilitate solution of the active ingredient using dilute acid or alkali or by the addition of suitable buffer salts. Antioxidants and metal chelating salts may also be included.

The solution is prepared, clarified and filled into appropriate sized ampoules sealed by fusion of the glass. The injection is sterilised by heating in an autoclave using one of the acceptable cycles. Alternatively the solution may be sterilised by filtration and filled into sterile ampoules under aseptic conditions. The solution may be packed under an inert atmosphere of nitrogen.

We claim:

1. A compound of formula (I)

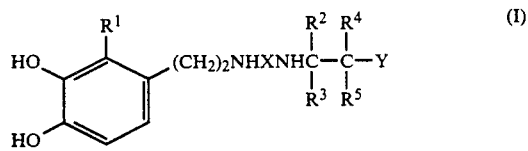

or a physiologically acceptable acid addition salt, metabolically labile ester or solvate thereof in which $R^1$ represents a halogen atom or a methyl, ethyl, n-propyl or n-butyl group;

$R^2$, $R^3$, $R^4$ and $R^5$ each represent hydrogen atoms or one or two of $R^2$, $R^3$, $R^4$ and $R^5$ represent a methyl or ethyl group X represents a $C_{4-7}$ alkylene chain optionally substituted by one or more $C_{1-4}$ alkyl or hydroxyl groups; or optionally containing one or two double or triple bonds; or optionally interrupted by an oxygen or sulphur atom, or by a sulphone ($-SO_2-$) or urea ($-NHCONH-$) group; and Y represents a phenyl ring optionally carrying one to three substituents selected from hydroxyl, $C_{1-4}$-alkyl, $C_{1-4}$alkoxy, amino, carboxamido, $C_{1-4}$alkyl-sulphonylamino and nitro groups and halogen atoms with the proviso that when X is a $C_{4-7}$ alkylene chain optionally containing one double bond then Y cannot represent phenyl or phenyl carrying one substituent which is halogen.

2. A compound according to claim 1 in which $R^1$ is methyl group, an ethyl group or a chlorine atom.

3. A compound according to claim 1 in which $R^2$, $R^3$, $R^4$ and $R^5$ each represent hydrogen atoms.

4. A compound according to claim 1 in which X represents a $C_{5-7}$ alkylene chain optionally substituted by one alkyl group or a hydroxyl group, or a $C_6$ alkylene chain containing one or two double bonds, or a $C_6$ alkylene chain interrupted by an oxygen or sulphur atom or by a sulphone ($-SO_2-$) group.

5. A compound according to claim 1 in which Y represents a group of formula (II)

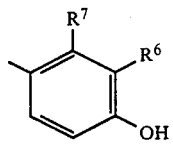

where $R^6$ represents a hydrogen atom or a group $CONH_2$ and $R^7$ is hydrogen, or $R^6$ represents a hydroxyl group and $R^7$ is a hydrogen or halogen atom or a $C_{1-4}$ alkyl group.

6. A compound according to claim 5 in which $R^6$ represents a hydroxyl group and $R^7$ represents a methyl or ethyl group.

7. A compound according to claim 1 in which X represents a $C_{5-7}$ alkylene chain and Y is a group of formula (IIa)

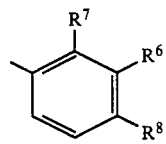

where $R^6$ and $R^8$, which may be the same of different, each represent a hydrogen atom or a hydroxy group (provided that at least one or $R^6$ and $R^8$ represent hydroxy) and $R^7$ represents a hydrogen atom or a halogen atom, or a $C_{1-4}$ alkyl group.

8. A compound selected from:
4,4'-[sulphonylbis[(3,1-propanediylimino)-2,1-ethanediyl]]bis[3-ethyl-1,2-benzenediol];
4,4'-[thiobis[(3,1-propanediylimino)-2,1-ethanediyl]-]bis[3-ethyl-1,2-benzenediol];
4,4'-[1,6-hexanediylbis(imino-2,1-ethanediyl)]bis[3-ethyl-1,2-benzenediol]; and
4-[2-[6-[2-(3,4-dihydroxy-2-methylphenyl)ethylamino]-hexylamino]ethyl]-3-ethyl-1,2-benzenediol
and physiologically acceptable salts thereof.

9. A compound according to claim 1 in which $R^1$ represents a methyl, ethyl, n-propyl or n-butyl group, $R^2$, $R^3$, $R^4$ and $R^5$ each represent hydrogen atoms or one or two of $R^2$, $R^3$, $R^4$ and $R^5$ represent a methyl or ethyl group, X represents a $C_{5-7}$ alkylene chain, and Y represents a phenyl ring carrying one to three substituents selected from hydroxyl, $C_{1-4}$ alkyl, $C_{1-4}$ alkoxy, amino and nitro groups and halogen atoms with the proviso that Y cannot represent phenyl carrying one substituent which is halogen.

10. A compound according to claim 1 in which $R^1$ represents a fluorine, chlorine, bromine or iodine atom, $R^2$, $R^3$, $R^4$ and $R^5$ each represent hydrogen atoms or one or two of $R^2$, $R^3$, $R^4$ and $R^5$ represent a methyl or ethyl group, X represents a $C_{5-7}$ alkylene chain, and Y represents a phenyl ring carrying one to three substituents selected from hydroxyl, $C_{1-4}$ alkyl, $C_{1-4}$ alkoxy, amino and nitro groups and halogen atoms with the proviso that Y cannot represent phenyl carrying one substituent which is halogen.

11. A pharmaceutical composition for the treatment or prophylaxis of renal insufficiency or cardiovascular disorders which comprises an effective amount to alleviate or for prophylaxis of said condition of at least one compound of general formula (I) as defined in claim 1 or a physiologically acceptable acid addition salt, metabolically labile ester or solvate thereof, together with a physiologically acceptable carrier or diluent.

12. A method of therapy or prophylaxis of renal insufficiency or cardiovascular disorders in a patient which comprises administering to said patient an effective amount to alleviate or for prophylaxis of said condition of a compound of general formula (I) as defined in claim 1 or a physiologically acceptable acid addition salt, metabolically labile ester or solvate thereof.

* * * * *